US008622968B2

(12) United States Patent
Watanabe et al.

(10) Patent No.: US 8,622,968 B2
(45) Date of Patent: *Jan. 7, 2014

(54) GASTROSTOMY TUBE EXTENSION DEVICE

(75) Inventors: Motonori Watanabe, Fukuroi (JP); Kazuhiro Abe, Fukuroi (JP); Katsuki Nagata, Fukuroi (JP)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/408,603

(22) Filed: Feb. 29, 2012

(65) Prior Publication Data

US 2012/0220946 A1 Aug. 30, 2012

Related U.S. Application Data

(63) Continuation of application No. 11/631,831, filed as application No. PCT/EP2005/004659 on Apr. 29, 2005, now Pat. No. 8,147,454.

(30) Foreign Application Priority Data

Apr. 30, 2004 (JP) ................................ 2004-135310

(51) Int. Cl.
*A61M 5/178* (2006.01)
*A61M 5/32* (2006.01)
(52) U.S. Cl.
USPC ....................... 604/164.04; 604/174; 604/910
(58) Field of Classification Search
USPC ....................... 604/164.03, 164.04, 174, 910, 604/104–109, 164.01, 165.01–165.03, 177, 604/178
See application file for complete search history.

(56) References Cited

U.S. PATENT DOCUMENTS

| 3,261,357 | A | * | 7/1966 | Roberts et al. ................ 604/105 |
| 3,397,699 | A | | 8/1968 | Kohl |
| 4,861,334 | A | | 8/1989 | Nawaz |
| 4,944,732 | A | | 7/1990 | Russo |
| 5,073,166 | A | | 12/1991 | Parks et al. |

(Continued)

FOREIGN PATENT DOCUMENTS

| EP | 0824929 A2 | 2/1998 |
| JP | 2003-275325 A | 9/2003 |
| WO | 97/34552 A1 | 9/1997 |
| WO | 02/066108 A1 | 8/2002 |

OTHER PUBLICATIONS

European Exam Report for EP 05737092.6 dated Jan. 19, 2009, 3 pgs.

(Continued)

*Primary Examiner* — Nicholas Lucchesi
*Assistant Examiner* — Jenna Zhang

(57) ABSTRACT

A gastrostomy tube extension device which can facilitate the insertion or removal operation in and from the patient, and increase the simplicity of manufacture. A gastrostomy tube extension device for inserting or taking out the gastrostomy tube into/from the patient includes a rod, a fixing member, and an engaging member. The rod is formed of a rod-shaped member with engaging stepped portions. The fixing member is capable of moving along the longitudinal direction of the rod, and an engaging projection which can be fixed to the tube member is formed on the peripheral surface of the fixing member. The engaging member includes a lower engaging portion engageable with the engaging projection and an upper engaging portion which is engageable with the engaging stepped portion This assembly allows the extension to be locked.

13 Claims, 22 Drawing Sheets

(56) References Cited

U.S. PATENT DOCUMENTS

| | | | |
|---|---|---|---|
| 5,080,650 A | | 1/1992 | Hirsch et al. |
| 5,356,382 A | * | 10/1994 | Picha et al. .................. 604/105 |
| 5,792,119 A | | 8/1998 | Marx |
| 5,855,569 A | | 1/1999 | Komi |
| 5,989,225 A | * | 11/1999 | Bodicky et al. .............. 604/174 |
| 6,093,173 A | | 7/2000 | Balceta et al. |
| 6,231,549 B1 | | 5/2001 | Noecker et al. |
| 6,322,538 B1 | | 11/2001 | Elbert et al. |
| 6,743,207 B2 | | 6/2004 | Elbert et al. |
| 6,767,340 B2 | | 7/2004 | Willis et al. |
| 2002/0165553 A1 | * | 11/2002 | Elbert et al. .................. 606/108 |
| 2004/0059293 A1 | | 3/2004 | Chu et al. |
| 2005/0085771 A1 | | 4/2005 | Lyon |
| 2007/0287962 A1 | | 12/2007 | Watanabe et al. |
| 2008/0208208 A1 | | 8/2008 | Nagata et al. |

OTHER PUBLICATIONS

European Search Report for EP 12156709.3 dated Mar. 23, 2012, 5 pgs.

Office action issued Oct. 5, 2009 in related U.S. Appl. No. 11/631,831 now issued as Patent No. 8,147,454—14 pgs.

Response filed Jan. 21, 2010 to Office Action dated Oct. 5, 2009 regarding related U.S. Appl. No. 11/631,831 now issued as Patent No. 8,147,454—18 pgs.

Office action issued Mar. 30, 2010 in related U.S. Appl. No. 11/631,831 now issued as Patent No. 8,147,454—15 pgs.

Response filed May 25, 2010 to Office Action dated Mar. 30, 2010 regarding related U.S. Appl. No. 11/631,831 now issued as Patent No. 8,147,454—9 pgs.

Advisory Action issued Jun. 9, 2010 from related U.S. Appl. No. 11/631,831 now issued as Patent No. 8,147,454—3 pgs.

Response filed Jun. 29, 2010 to Advisory Action dated Jun. 9, 2010 regarding related U.S. Appl. No. 11/631,831 now issued as Patent No. 8,147,454—8 pgs.

Office action issued Oct. 14, 2010 in related U.S. Appl. No. 11/631,831 now issued as Patent No. 8,147,454—13 pgs.

Response filed Jan. 14, 2011 to Office Action dated Oct. 14, 2010 regarding related U.S. Appl. No. 11/631,831 now issued as Patent No. 8,147,454—13 pgs.

Office action issued Feb. 15, 2011 in related U.S. Appl. No. 11/631,831 now issued as Patent No. 8,147,454—13 pgs.

Response filed Apr. 7, 2011 to Office Action dated Feb. 15, 2011 regarding related U.S. Appl. No. 11/631,831 now issued as Patent No. 8,147,454—11 pgs.

Office action issued Apr. 26, 2011 in related U.S. Appl. No. 11/631,831 now issued as Patent No. 8,147,454—11 pgs.

Response filed Jul. 22, 2011 to Office Action dated Apr. 26, 2011 regarding related U.S. Appl. No. 11/631,831 now issued as Patent No. 8,147,454—10 pgs.

Office action issued Aug. 18, 2011 in related U.S. Appl. No. 11/631,831 now issued as Patent No. 8,147,454—13 pgs.

Response filed Nov. 15, 2011 to Office Action dated Aug. 18, 2011 regarding related U.S. Appl. No. 11/631,831 now issued as Patent No. 8,147,454—9 pgs.

Examination Report dated Mar. 13, 2013 issued by the Australian Patent Office in counterpart Australian Patent Application No. 2011226935 (3 pages).

Examination Report dated Mar. 6, 2013 issued by the European Patent Office in counterpart European Patent Application No. 12156709.3.

\* cited by examiner

GASTROSTOMY TUBE EXTENSION DEVICE

CROSS REFERENCE TO RELATED APPLICATIONS

This application is a continuation of and claims the benefit of priority under 35 U.S.C. §120 to copending U.S. patent application Ser. No 11/631,831, filed Aug. 6, 2007, which is a national stage application under 35 U.S.C. §371 of International Application No. PCT/EP2005/004659, filed Apr. 29, 2005, which claims priority to Japanese Patent Application No. 2004-135310, filed Apr. 30, 2004, the entirety of each of which is hereby incorporated by reference for all purposes.

TECHNICAL FIELD

The present invention relates to a gastrostomy tube extension device for inserting or removing a gastrostomy tube used for feeding fluid substances such as liquid food into a stomach of a patient into/from the patient' body.

BACKGROUND ART

Hitherto, feeding of the fluid substances such as the liquid food or nutrient preparation using the gastrostomy tube has been carried out for persons whose capability to take food orally by their own abilities is deteriorated due to aging or diseases (hereinafter referred to as a "patient"). The gastrostomy tube includes a stomach interior fixing member to be installed on the inside of a stomach wall at a hole (a gastric fistula) for dietary intake formed on the abdomen of the patient, and a tube member connected to the stomach interior fixing member at the distal portion thereof and extends through the hole toward the outside of the patient at the proximal portion. When inserting the gastrostomy tube into the hole formed on the patient's body, the operation for insertion is performed by a rod-shaped extender, such as that disclosed in JP-A-2003-275325.

The stomach interior fixing member of the gastrostomy tube is formed into a bowl shape, with a through hole through which the extender can be passed through a part in the vicinity of a joint member joining the extender with the tube member. When the extender is passed through the through hole of the gastrostomy tube from the outside and is pushed toward the distal portion of the stomach interior fixing member, the distal portion of the extender is hooked on the inner side of the stomach interior fixing member, and is used to push the interior fixing member into an elongated and narrowed state. Since the stomach interior fixing member in the narrowed state can pass through the hole formed on the abdominal part of the patient, the gastrostomy tube can be placed in the hole simply by inserting the stomach interior fixing member into the stomach. After inserting the stomach interior fixing member into the stomach, the extender is removed from the body.

When the gastrostomy tube is to be removed from the body, the user simply by pulls on the tube member. In this case, the stomach interior fixing member is bent and contracted in a certain direction by the through hole, allowing it to be removed from the hole.

However, in the gastrostomy tube described above, resistance of the stomach interior fixing member is significant and hence the removal is difficult, painful, and likely to cause damage to the abdominal part of the patient. In addition, when inserting the gastrostomy tube into the hole formed on the patient's body, it is necessary for the user to manually press the extender against the stomach interior fixing member, and maintain this pressure constantly throughout the procedure. Complexity places a large burden on the operator.

DISCLOSURE OF THE INVENTION

In order to solve the above-described problems, it is an object of the present invention to provide a gastrostomy tube extension device which can easily be inserted or taken out.

In order to achieve the above-described object, the gastrostomy tube extension device includes: an extender formed of a rod-shaped member which can be inserted into a tube member of the gastrostomy tube and can elongate and narrow the stomach interior fixing member of the gastrostomy tube by pushing the distal end of the stomach interior fixing member in the distal direction with the distal end of the extender. A fixing member is fixed to the outside end of the tube member and inserted into the tube member which is capable of moving along the longitudinal direction of the extender. An engaging portion is engageable with the fixing member; and an engaging member having a holding portion, to be held by hand, elongates and narrows the stomach interior fixing member when pulled in the direction of the outside end of the tube in a state in which the extender is inserted into the tube member and the engaging portion is engaged with the fixing member fixed to the outside end of the tube member.

The fixing member is to be fixed on the outside end of the tube member which is located out of the body, and the engaging member having an engaging portion, is capable of being engaged to the fixing member. The fixing member is capable of moving along the longitudinal direction of the extender. When the extender is inserted into the tube member and the tube member and the fixing member are engaged with each other, the stomach interior fixing member can be narrowed by holding the holding portion and pulling the engaging member in the proximal direction The gastrostomy tube can be removed easily without damaging the abdomen of the patient. When the gastrostomy tube is inserted into the hole on the patient, the thickness of the stomach interior fixing member can be easily held constant, since the holding portion is provided on the engaging member. In this manner, the operator who performs the insertion or removal of the gastrostomy tube need concentrate only on the insertion or removal operation itself, without paying attention to the extended state of the gastrostomy tube, even when using only one hand, thus facilitating insertion and removal of the gastrostomy tube. The holding portion may be of various shapes as long as it can be hand-held for operation.

Another structural characteristic of the gastrostomy tube extension device according to the present invention is that the fixing member is hollow cylindrical, capable of moving along the longitudinal direction of the extender when surrounding the outer peripheral surface of the extender, and the cylindrical member is provided with a fixed portion to be fixed at the outside end of the tube member, and an engaged portion to be engaged the engaging portion of the engaging member. In this arrangement, since the fixing member moves precisely along the longitudinal direction of the extender, the direction of extension of the gastrostomy tube and the longitudinal direction of the extender are aligned in a straight line. Therefore, deformation in the direction of extension of the gastrostomy tube is prevented, and the insertion or removal operation can be performed while keeping the gastrostomy tube in a proper state.

In another arrangement the fixed portion is formed with a projection which is formed on the outer peripheral surface of the cylindrical member so as to be capable of being press-fitted into the tube member. In other words, the fixed portion can be fixed to the tube member merely by inserting the cylindrical member into the tube member, which improves the ease of use.

By employing a longer cylindrical member, the contact surface with respect to the cylindrical member increases, and hence excessive extension of the tube member does not occur, and a force exerted to the extender or the engaging member is efficiently used for extension of the stomach interior fixing member. The projection formed on the cylindrical member may be either single or plural.

The projection which comprises the fixed portion may be formed on the outer peripheral surface of the cylindrical member all along the circumference thereof, having a tapered portion with a diameter which is smaller toward the distal end when press-fitted into the tube member and gradually increases toward the proximal end. In this arrangement, the fixed portion can be more easily inserted into the tube member, and after fixing the tube member and the fixed portion, it is difficult to disconnect the fixed portion from the tube member. Therefore, the gastrostomy tube can be extended in a stable state.

In another arrangement, the engaged portion may comprise a projection which constitutes the fixed portion, and the engaging portion of the engaging member is adapted to engage the outer peripheral surface of the tube member, through which the cylindrical member is press-fitted to fix the fixed portion, at a portion corresponding to the engaged portion. In this arrangement, the fixed portion to be fixed to the tube member of the fixing member and the engaged portion to be engaged to the engaging member are a unitary structure, thus simplifying the device. In addition, since the engaging portion of the engaging member engages the outer peripheral surface of the tube member which fixes the fixed portion, the engaging portion presses the tube member to ensure fixation between the tube member and the fixed portion.

A positioning portion may be provided on the peripheral surface of the proximal portion of the extender, and a positioned portion which can engage the positioning portion may be provided on the engaging member so that with the extender inserted into the tube member, the stomach interior fixing member is elongated and narrowed when the fixing member is engaged with the engaging portion and the positioning portion is engaged with the positioned portion respectively. In this arrangement, after engagement of the fixing member with the engaging portion and the positioning portion with the positioned portion respectively, even when the operator releases his/her hand from the holding portion of the engaging member, the stomach interior fixing member is maintained at a constant narrow width. Therefore, the operator who performs the inserting or removal operation of the gastrostomy tube can concentrate only on the insertion or removal operation without paying attention to the extended state of the gastrostomy tube.

A plurality of positioning portions may be formed along the axial direction of the extender. In this arrangement, the extended state of the gastrostomy tube can be modified by selecting the positioning portion of the extender to which the positioned portion of the engaging member is engaged as needed. Accordingly, versatility is provided, and hence one type of gastrostomy tube extension device may be sufficient. In this arrangement, adaptation can be made to change in the expansion or other physical properties of the gastrostomy tube.

For example, when inserting the gastrostomy tube into the hole on the patient, the positioned portion of the engaging member is engaged with the positioning portion which provides the minimum extension of the gastrostomy tube before operation. Then, when the gastrostomy tube is taken out from the hole on the patient after having been left in the patient's body for a predetermined period, the operation can be performed with the positioned portion engaged with another positioning portion. Accordingly, the operation can be performed with the gastrostomy tube expanded optimally for each operation.

The extender may comprise a rod-shaped member which can be inserted into the tube member and can elongate and narrow the stomach interior fixing member by pushing the distal end of the stomach interior fixing member toward the distal side by the distal end of the extender.

In this arrangement, the structure of the fixing portion can be greatly simplified. For example, a structure in which a cylindrical or ring-shaped member is fixed on the outer peripheral surface of the tube member may be sufficient. It is also possible to provide a recess or the like on the outer peripheral surface of the tube member as a fixing portion. Therefore, manufacturing of the fixing portion is facilitated, and the cost of the gastrostomy tube extension device can be reduced. In this case, the operator can operate the device by holding the fixing portion formed on the tube member by hand while the extender is inserted in the gastrostomy tube. It is also possible to provide an engaging member including an engaging portion capable of engaging the fixing member and the holding portion for holding by hand to operate the device, elongating the stomach interior fixing member when the holding portion is pulled in the direction of the outside portion of the tube member when the extender is inserted into the tube member and the engaging portion is engaged with the fixing member fixed to the outside end of the tube member.

In this case as well, it is possible to form a positioning portion on the peripheral surface of the proximal portion of the extender, and provide a positioned portion, which is capable of engaging the positioning portion, on the engaging member, so that when the extender is inserted into the tube member, the stomach interior fixing member can be elongated and narrowed when the fixing portion is engaged with the engaging portion and the positioning portion is engaged with the positioned portion respectively. In addition, a plurality of positioning portions can be provided along the axial direction of the extender.

The device may include a movable fixing member comprising a fixing portion which is capable of being fixed to the outside end of the tube member and a holding portion to be held by hand for operation of the device, and which is movable along the longitudinal direction of the extender inserted into the tube member.

In this case, the fixing portion to be fixed to the outside end of the tube member and the holding portion held by hand for operation of the device are provided on a single movable fixing member. The movable fixing member is movable along the longitudinal direction of the extender. Therefore, when the extender is inserted into the tube member, by holding the holding portion and pulling the movable fixing member in the direction opposite to insertion of the extender, the stomach interior fixing member can be narrowed. In this arrangement as well, the gastrostomy tube can be taken out without damaging the abdomen of the patient, and the insertion of the gastrostomy tube into the hole on the patient or the removal operation of the gastrostomy tube from the hole can be performed easily. In this case, since the number of members which constitute the gastrostomy tube extension device is reduced, manufacture can be facilitated and the cost is reduced.

Furthermore, the fixing portion of the movable fixing member may be hollow cylindrical, movable along the longitudinal direction of the extender when surrounding the outer peripheral surface of the extender, and the cylindrical member can be provided with the fixed portion to be fixed on the outside end of the tube member. Also, the fixed portion may be formed on the outer peripheral surface of the cylindrical member, comprising projections which can be press-fitted into the tube member. In addition, a projection which constitutes a fixed portion may be formed on the outer peripheral surface of the cylindrical member all along the circumference thereof, and may be formed of a tapered portion with a cross section diameter which is smaller toward the distal end when press-fitted into the tube member and gradually increases toward the proximal end. The projection may be single or plural.

In this arrangement, since the direction of movement of the movable fixing member matches the longitudinal direction of the extender, there is no difference between the direction of extension of the gastrostomy tube and the direction of movement of the movable fixing member, and hence the insertion or removal-operation can be performed with the gastrostomy tube extended in an adequate state. Also, a stable fixation between the tube member and the fixed portion of the movable fixing member is further ensured. In addition, when fixing the tube member to the fixed portion, the cylindrical member can easily be inserted into the tube member, and after having inserted the cylindrical member into the tube member and fixing the tube member to the fixed portion, it is difficult to disconnect the cylindrical member from the tube member.

The gastrostomy tube extension device according to the present invention may comprise a tightening member for tightening the outer peripheral surface of the tube member through which the cylindrical member is press-fitted in order to strengthen the fixation of the fixed portion to the tube member. The tightening member in this case may be provided by forming a threaded portion on the cylindrical member of the fixed portion, and providing a round tubular member formed with a thread at the upper portion of the inner periphery thereof which can be attached to and detached from the above threaded portion, and the outer peripheral surface of the tube member can be tightened by the lower portion of the inner peripheral surface of this member. It is also possible to provide a tightening member in the form of a clip. The tightening member if of particular significance when the length of the cylindrical member is set to be short.

Where a movable fixing member is provided with a positioned portion which can engage the positioning portion, which may be a plurality of fixing portions, the positioning portions are a plurality of projections formed along the axial direction of the extender and the positioned portion is constituted of the cylindrical member formed of resilient material, so that the positioned portion can be engaged to one specific positioning portion.

In this arrangement, the stomach interior fixing member can be maintained in a constant narrow width, thus improving the ease of operation. Also, the narrowness of the gastrostomy tube can be modified. In addition, since engagement between the positioned portion and the positioning portion can be achieved simply by inserting the cylindrical member formed with the positioned portion onto the positioning portion on the extender, the ease of operation is further increased, and the structure is simple and low-cost.

BEST MODE FOR CARRYING OUT THE INVENTION (First Embodiment)

Referring to drawings 1 through 6, a first embodiment of the present invention will be described. FIG. 1 shows a state in which a gastrostomy tube extension device 20 according to the first embodiment of the present invention is mounted to a gastrostomy tube 10. The gastrostomy tube 10 includes a tube member 11 formed of polyurethane as shown in FIG. 2, and a stomach interior fixing member 12 connected to the lower end of the tube member 11. In the following description, the side of the tube member 11 is referred to as the upper side, and the side of the stomach interior fixing member 12 is referred to as the lower side.

The interior of the tube member 11 is formed into a feed path 13 of a hole for allowing fluid substances such as liquid food to pass through. The tube member 11 has elasticity, and hence is extended when pulled, and returns to its original state when the pulling force is removed. The tube member 11 has a function to block the hole by being fixed in the hole when the gastrostomy tube 10 is placed in the hole (not shown) formed on the abdominal part of a patient, and prevent the liquid or the like from leaking from inside the stomach.

The stomach interior fixing member 12 includes a cylindrical joint member 14 joined to the lower end of the tube member 11, and an inner holding strip 15 joined to the opening edge at the lower end of the joint member 14. The joint member 14 is formed into a cylindrical shape so as to cover the lower end portion of the outer peripheral surface of the tube member 11, and is fixed to the tube member 11 in a state in which the lower end of the tube member 11 is inserted in the joint member 14. The upper portion of the inner holding strip 15 is joined to the periphery of the lower end of the joint member 14, and constitutes a contact portion 15a of substantially dome shape which comes into contact with the stomach wall when the stomach interior fixing member 12 is positioned inside the stomach. The lower portion of the inner holding strip 15 is comprised of four band-shaped joint members 15b joined to the lower edge of the contact portion 15a and a connecting portion 15c for connecting the distal end of the respective joined members 15b.

Formed at the center portion of the upper surface of the contact portion 15a is a hole which communicates with the feed path 13 of the tube member 11. The center portion of the upper surface of the contact portion 15a with which the stomach wall comes into contact is formed into a flat shape. The four joint members 15b are provided at regular intervals in the circumferential direction at the lower end of the contact portion 15a, and are separated into four directions from the lower edge of the contact portion 15a downward respectively, and then converged at a position below the center axis of the tube member 11 to constitute the connecting portion 15c, and are there fixed together.

In other words, the connecting portion 15c connects the respective joint members 15b with each other by joining the lower end portions of the respective joint members 15b, and is positioned at a lower location of the center axis of the tube member 11 by the respective joint members 15b. Therefore, the inner holding strip 15 is formed into substantially a spherical shape as a whole with the pairs of opposing joint members 15b, 15b, and the outline of the contact portion 15a forms a circle respectively.

The contact portion 15a and the respective joint members 15b are formed of soft elastic material having flexibility, and are maintained in a substantially spherical shape as a whole as shown in FIG. 1 and FIG. 2 in the normal state by this elasticity. However, when the connecting portion 15c is pressed downward, it is expanded to a straight elongated state. In comparison with the portions of the contact portion 15a which correspond to the respective joint members 15b, the portions other than the above-described portions are thinner from the lower end to the upper end.

Therefore, the contact portion 15a is constructed of the portions extending from the joint members 15b and the thinned portions therebetween, and hence when the connecting portion 15c is pulled downward, it is folded to specified shape and is easily narrowed into an elongated shape. The connecting portion 15c is formed at the center thereof with a hole, and an engaging portion 16 of a short cylindrical shape is fixed to this hole. The engaging portion 16 is formed at the center thereof with a hole 16a for positioning the distal portion of a rod (see FIG. 3) 21 described later. The stomach interior fixing member 12 configured as described above has a function to be fixed to the inner surface of the stomach wall of the patient and prevent the gastrostomy tube 10 from being separated from the patient's body.

The gastrostomy tube extension device 20 according to the first embodiment includes a rod 21 as the extender, a fixing member 22, and an engaging member 23 according to the present invention as shown in FIG. 3. The rod 21 has a main body 21a formed of a rod-shaped member, possibly of stainless steel, and a holding portion 21b, possibly formed of plastic. The main body 21a is provided with a pushing portion 29, possibly of plastic, attached at the distal end thereof. The pushing portion 29 includes a secured portion 29a fixed to the main body 21a in a state of covering the peripheral surface of the lower end portion of the main body 21a, and a push-insertion piece 29b extending distally from the lower end of the secured portion 29a.

The outer diameter of the secured portion 29a is set to be larger than the diameter of the hole 16a of the engaging portion 16 provided on the gastrostomy tube 10, and the diameter of the push-insertion piece 29b is set to be smaller than the diameter of the hole 16a. Therefore, when the rod 21 is inserted downward from an upper opening 13a of the feed path 13 of the tube member 11, the push-insertion piece 29b is inserted into the hole 16a, and the secured portion 29a is located in such a manner that its lower surface is positioned on the upper surface of the engaging portion 16. Accordingly, when the rod 21 is pressed downward into the gastrostomy tube 10, the stomach interior fixing member 12 extends and narrows.

A cylindrical portion 24 configured integrally with the holding portion 21b is formed on the upper portion of the main body 21a and below the holding portion 21b so as to cover the circumference of the main body 21a, and engaging stepped portions 24a as the positioning portions of the present invention are formed on the outer peripheral surface thereof. Each engaging stepped portion 24a is a ring-shaped projection of substantially triangular shape in vertical cross-section formed on the peripheral surface of the cylindrical portion 24 along the circumference thereof, and three of these engaging stepped portions 24a are formed at intervals along the axial direction of the cylindrical portion 24. The upper surface of the holding portion 21b may be formed into a curved surface depressed into an arcuate shape for allowing the operator's hand or finger, in particular, the thumb, to fit for operation.

The fixing member 22 may be formed of stainless steel, and a main body 22a is formed into a cylindrical shape. The main body 22a is formed with an engaging projection 25 on the outer peripheral surface on the upper end of the main body 22a. The engaging projection 25 includes a tapered portion 25a the diameter of which is smaller toward its lower edge and gradually increases toward the top. The portion above the tapered portion 25a is formed so as to gradually decrease in diameter, so that a stepped portion is formed at the interface with the tapered portion 25a. The engaging projection 25 constitutes both the fixed portion and the engaged portion of the present invention. Formed on the upper end of the main body 22a is a ring-shaped holding portion 22b having the outer diameter larger than that of the main body 22a.

The fixing member 22 is mounted to the main body 21a by covering the outer peripheral surface of the main body 21a of the rod 21 as shown in FIG. 4, and in this state, it is movable along the longitudinal direction of the main body 21a. The main body 22a of the fixing member 22 is adapted to be inserted into the feed path 13 of the tube member 11, and the engaging projection 25 is adapted to be press-fitted into the feed path 13 of the tube member 11. When the main body 22a is inserted into the tube member 11, the fixing member 22 is fixed to the tube member 11 by the engagement between the tube member 11 and the engaging projection 25.

The engaging member 23 may be formed into a shape as shown in FIG. 3 by machining a stainless steel plate, and includes a lower engaging portion 26 as the engaging portion of the present invention, and an upper engaging portion 27 as the positioned portion of the present invention. The lower engaging portion 26 and the upper engaging portion 27 are connected by a joint strip 28 of a vertically elongated rectangular plate shape. The lower engaging portion 26 includes a holding strip 26a of substantially U-shape in plan view, and a pair of claw portions 26b, and the holding strip 26a is formed so as to extend from the lower end of the joint strip 28 horizontally toward the near side of the drawing and orthogonally to the joint strip 28.

The claw portions 26b are provided in parallel with the holding strip 26a so as to extend from both sides of the lower end portion of the joint strip 28, orthogonally to the joint strip 28 and at a distance from the holding strip 26a. The inside of the substantially U-shape of the holding strip 26a is formed into a recess which can clamp the portion corresponding to the tapered portion 25a of the engaging projection 25 in the state of being press-fitted into the tube member 11 as shown in FIG. 1.

The upper engaging portion 27 is formed so as to extend from the upper end of the joint strip 28 horizontally toward the near side of the drawing and orthogonally to the joint strip 28, and is configured by a laterally elongated part extending from both sides of the joint strip 28. The length of the upper engaging portion 27 in the fore-and-aft direction is set to be short, and is formed at the front center with an engaging recess 27a which can engage the respective engaging stepped portions 24a. A pair of projections 27b for preventing the engagement with the engaging stepped portion 24a from being released project downward at both sides of the engaging recess 27a and at the front portion of the upper engaging portion 27. In addition, both side portions of the upper engaging portion 27 are curved downwardly so as to facilitate operation performed with the operator's hand hooked thereon, and the distal portion of the holding strip 26a is curved upward so as to prevent engagement with the engaging projection 25 from being released.

The gastrostomy tube extension device 20 in this arrangement is used for inserting the gastrostomy tube 10 into the hole formed on the abdomen of the patient or taking out the same from the hole. The case of taking out the gastrostomy tube 10 from the hole will first be described here. FIG. 5 shows the gastrostomy tube 10a in use. The gastrostomy tube 10a has a long tube member 11a and includes a connecting member 17 for connecting a feeding tube (not shown) for feeding nutrient preparation into the gastrostomy tube 10a connected to the upper end thereof. The connecting member 17 includes two feeding ports 17a, 17b, and the feeding ports 17a, 17b are openable and closable by corresponding lids 18a, 18b, respectively.

The lower portion of the gastrostomy tube 10a constitutes the gastrostomy tube 10 described above, with the lower portion of the tube member 11a positioned at the hole formed between the abdominal wall and the stomach wall of the patient and the stomach interior, and with fixing member 12 placed in the patient's stomach. When feeding fluid substance such as liquid food or nutrient preparation to the patient, the predetermined feeding ports 17a, 17b at the connecting member 17 at the proximal end of the tube member 11a extending toward the outside the body are opened and the feeding tube is connected to the feeding ports 17a, 17b.

In this state, nutrient preparation is fed to the patient with this feeding tube and the gastrostomy tube 10a. In this case, the fluid substance fed out of the lower opening of the tube member 11a enters into the stomach from the stomach interior fixing member 12 passing through the spaces between the joint members 15b. After use, the feeding tube is disconnected from the connecting member 17, and the feeding ports 17a, 17b are closed with the lids 18a, 18b. When replacement of the gastrostomy tube 10a is necessary after a predetermined period of use, the tube member 11a is cut at a position indicated by a broken line "a" in FIG. 5. Accordingly, the gastrostomy tube 10 remains in the patient's body.

Subsequently, as shown in FIG. 4, the rod 21 provided with the fixing member 22 attached thereto is inserted downward from the upper opening 13a of the tube member 11. In this case, the operator holds the holding portion 22b with his/her hand and presses the main body 22a of the fixing member 22 into the tube member 11 so that the engaging projection 25 is fixed to the upper end of the tube member 11. Then, the push-insertion piece 29b of the rod 21 is aligned with the engaging portion 16 of the stomach interior fixing member 12 and pushed into the hole 16a. Subsequently, the holding strip 26a of the lower engaging portion 26 is engaged with the outer peripheral surface of the tube member 11 at the engaging projection 25, and the engaging member 23 is connected to the rod 21 to which the gastrostomy tube 10 and the fixing member 22 are attached, in a state in which the main body 21a is positioned in the engaging recess 27a to obtain the state shown in FIG. 1.

Subsequently, in a state in which the operator holds the upper surface of the holding portion 21b by hand to prevent the push-insertion piece 29b from separating from the hole 16a, the operator hooks his fingers with the lower surface of the upper engaging portion 27 and pulls the engaging member 23 upward, so that the edge of the engaging recess 27a is engaged with the predetermined engaging stepped portion 24a, for example, the engaging stepped portion 24a located at the center. Accordingly, as shown in FIG. 6, the stomach interior fixing member 12 extends straight and is narrowed, and hence the tube member 11 and the stomach interior fixing member 12 form the shape similar to one single rod. In this case, not only the stomach interior fixing member 12, but also the tube member 11 is brought into an extended state.

The gastrostomy tube 10 and the gastrostomy tube extension device 20 are assembled in a state in which the engaging projection 25 is prevented from separating from the holding strip 26a by the curved portion at the distal end of the holding strip 26a, and the engaging stepped portion 24a of the rod 21 is prevented from coming apart from the engaging recess 27a by the projections 27b. Then, the gastrostomy tube 10 is taken out from the hole on the patient by pulling the rod 21 in a state in which the gastrostomy tube 10 is extended as shown in FIG. 6. In this case, since the stomach interior fixing member 12 is elongated and narrowed, the removal of the gastrostomy tube 10 can be performed smoothly.

When the gastrostomy tube 10 has been taken out from the patient, the operator hooks his/her fingers with the lower surface of the upper engaging portion 27, and pulls the engaging member 23 upward, whereby the engaging recess 27a is removed from the engaging stepped portion 24a and the holding strip 26a is removed from the engaging projection 25, so that the engaging member 23 is removed from the gastrostomy tube 10 and the rod 21. Then, the rod 21 is taken out from the gastrostomy tube 10 to complete the removal operation. The used gastrostomy tube 10 is disposed, and the gastrostomy tube extension device 20 is used again for the next process.

Since the gastrostomy tube extension device 20 according to the present embodiment is configured as described above, the rod 21 including the fixing member 22 attached thereto is inserted into the tube member 11 of the gastrostomy tube 10, so that the engaging projection 25 of the fixing member 22 is fixed to the upper end of the tube member 11. Then, the engaging member 23 is pulled upward in a state in which the lower engaging portion 26 is engaged with the outer peripheral surface of the tube member 11 at the engaging projection 25 to cause the upper engaging portion 27 to be engaged the predetermined engaging stepped portion 24a, whereby the stomach interior fixing member 12 is maintained in an narrowed state. Therefore, the operator who conducts a surgical operation can concentrate on the insertion or removal operation without paying attention to the extended state of the gastrostomy tube 10 for treatment. Consequently, the operation to insert the gastrostomy tube 10 into the hole on the patient or to take out the same from the hole is facilitated.

In this case, since the fixing member 22 is formed into a cylindrical shape, and hence moves along the longitudinal direction of the main body 21 of the rod 21, the operation can be facilitated, and an adequate extension of the gastrostomy tube 10 is achieved. In addition, since the fixing member 22 is fixed to the tube member 11 by the engaging projection 25, and the holding strip 26a of the engaging member 23 engages the engaging projection 25 so as to clamp the tube member 11, fixation of the fixing member 22 to the tube member 11 is further ensured. Furthermore, since the tube member 11 is brought into a firm contact with the outer peripheral surface of the main body 22a of the fixing member 22 when it is extended to a certain extent, and hence is prevented from excessively extending, a force to push the rod 21 is efficiently used for extension of the stomach interior fixing member 12.

Also, the distal end of the holding strip 26a of the lower engaging portion 26 is curved upward and hence it is hard for the engaging projection 25 to separate from the lower engaging portion 26, and the pair of the projections 27b are provided on the opening edge of the engaging recess 27a at the front portion of the upper engaging portion 27, so that it is hard for the engaging stepped portion 24a of the rod 21 to separate from the upper engaging portion 27. Therefore, the gastrostomy tube extension device 20 maintains the gastrostomy tube 10 in the extended state stably without accidental disconnection of the gastrostomy tube extension device 20 from the gastrostomy tube 10.

Furthermore, since the three of the engaging stepped portions 24 are provided at regular intervals, the gastrostomy tube 10 can be extended in three-step lengths. Therefore, versatility is provided, and hence insertion or removal operation of various types of gastrostomy tubes can be performed by one type of gastrostomy tube extension device 20. Since the engaging stepped portion 24a for engaging the engaging recess 27a can be selected according to the expansion or other physical properties of the gastrostomy tube 10, operation in the optimal state is achieved.

(Second Embodiment)

FIG. 7 through FIG. 9 show a gastrostomy tube extension device 30 according to a second embodiment of the present invention. A fixing member 32 provided on the gastrostomy tube extension device 30 includes an engaging projection 35 formed on the outer peripheral surface of the main body 32a at a position slightly lower than the center portion as shown in FIG. 9. The engaging projection 35 includes a tapered portion 35a, the diameter of which is smaller toward the distal end and gradually increases toward the proximal end, and a tapered portion 35b which is formed proximally to the tapered portion 35a so as to be vertically symmetric. Regarding the engaging member 33, the vertical length of a joint strip 38 is set to be longer than the engaging projection 35 of the fixing member 32 by a distance corresponding to the downward movement of the engaging projection 35 of the fixing member 32.

The structures of other portions of the gastrostomy tube extension device 30 are the same as the corresponding portions of the gastrostomy tube extension device 20. Therefore, the same parts are represented by the same reference numerals and their descriptions will be omitted. In this arrangement, in the gastrostomy tube extension device 30, the holding strip 26a of the engaging member 33 holds the portion of the tube member 11 lower than the center portion, and engages the engaging strip 35. Therefore, fixation of the fixing member 32 to the tube member 11 is further ensured. According to the gastrostomy tube extension device 30, operation for inserting the gastrostomy tube provided with a long tube as shown in FIG. 5 into the hole on the patient is facilitated. Other effects and advantages of the gastrostomy tube extension device 30 are the same as the aforementioned gastrostomy tube extension device 20.

(Third Embodiment)

FIG. 10 through FIG. 12 show a gastrostomy tube expansion device 40 according to a third embodiment of the present invention. In a rod 41 provided on the gastrostomy tube extension device 40, an engaging stepped portion 44a is formed of a ring-shaped projection formed on the outer peripheral surface of a cylindrical portion 44 having a semi-circular vertical cross-section, and five of those projections are formed along the axis of the cylindrical portion 44 at regular intervals.

As shown in FIG. 12, a fixing portion 42 is formed of a cylindrical member the diameter of which is set to be larger toward the lower edge, and gradually decreases toward the upper portion thereof, and is fixed to the outer peripheral surface of the tube member 11 of the gastrostomy tube 10 at the upper end portion thereof. The lower surface of the fixing portion 42 constitutes an engaging projection 45. A lower engaging portion 46 of an engaging member 43 is constituted of the frame body including a holding piece 46a and a claw portion 46b formed continuously and integrally with each other.

The structures of other portions of the gastrostomy tube extension device 40 are the same as the corresponding portions of the gastrostomy tube extension device 20. Therefore, the same parts are represented by the same reference numerals and descriptions thereof will not be made. In this arrangement, in the gastrostomy tube extension device 40, since the structure of the fixing portion 42 is extremely simplified, manufacture can be facilitated, and the cost is reduced. Also, since the operation for fixing the fixing portion 42 to the gastrostomy tube 10 is not necessary, the operation of the device during a surgical operation is simplified. Other effects and advantages of the gastrostomy tube extension device 40 are the same as the aforementioned gastrostomy tube extension device 20.

(Fourth Embodiment)

FIG. 13 shows a fixing portion 52 provided on the gastrostomy tube expansion device according to a fourth embodiment of the present invention. The fixing portion 52 includes an engaged portion 53 which has the same structure as the aforementioned fixing portion 42 and an inner reinforcing member 54. The inner reinforcing member 54 is formed by molding resin, and includes a cylindrical portion 54a which can be press-fitted into the tube member 11 and a flange-shaped holding portion 54b provided at the upper end of the cylindrical portion 54a.

The structures of other portions of the gastrostomy tube extension device provided with the fixing portion 52 are the same as the corresponding portions of the gastrostomy tube extension device 40 (third embodiment). In this arrangement, the cylindrical portion 54a of the inner reinforcing member 54 comes into firm contact with the inner peripheral surface of the tube member 11, so that extension of the tube member 11 is restrained. Accordingly, the tube member 11 is prevented from becoming damaged. Other effects and advantages of the gastrostomy tube extension device provided with the fixing portion 52 are the same as the aforementioned gastrostomy tube extension device 40.

(Fifth Embodiment)

FIG. 14 and FIG. 15 show a fixing portion 62 provided on the gastrostomy tube extension device according to a fifth embodiment of the present invention. The fixing portion 42 includes an engaged portion 63 having substantially the same shape as the aforementioned fixing portion 42 and being smaller than the fixing portion 62 and a connector 64 detachably engaging the engaged portion 63. A connector 64 includes a pair of joint strips 66a, 66b which are capable of rotating with respect to each other about a hinge joint 65, and the distal ends of the joint strips 66a, 66b are provided with engaging portions 67a, 67b which can be connected to and detached from each other through one-touch operation. The joint strips 66a, 66b are configured to form a cylindrical member which can cover the outer peripheral surface of the tube member 11 when the engaging portions 67a, 67b are engaged.

The joint strips 66a, 66b are formed on the inner circumference surface with an engaging groove 68 which can engage the engaged portion 63, and the joint strips 66a, 66b are formed with a pair of engaging projections 69a, 69b on the outer peripheral surface thereof. The engaging projections 69a, 69b are adapted to be capable of engaging the lower engaging portion 26 provided on the aforementioned engaging member 23. The structures of other portions of the gastrostomy tube extension device provided with the fixing portion 62 are the same as the corresponding portions of the gastrostomy tube extension device 20 (first embodiment). In this structure, engagement between the engaged portion 63 which is fixed to the tube member 11, and the engaging member 23 can further be ensured. Since the engaged portion 63 is a small member, resistance generated when the portion of the tube member 11 formed with the engaged portion 63 is passed through the hole on the patient is small, and hence it can easily be passed through. Other effects and advantages of the gastrostomy tube extension device provided with the fixing portion 62 are the same as the aforementioned gastrostomy tube extension device 20.

(Sixth Embodiment)

FIG. 16 shows an engaged portion 72 as the fixing portion provided on the gastrostomy tube extension device according to a sixth embodiment of the present invention. The engaged portion 72 includes a recess formed on the outer peripheral surface of the tube member 11. The recess which constitutes the engaged portion 72 is formed into a tapered-shape, the diameter of which is larger toward the lower end and gradually decreases toward the upper end, and the upper end portion is formed with a stepped portion 72a. The lower engaging portion provided on the engaging member (not shown) is provided with a narrow holding strip which can engage the stepped portion 72a.

The structures, effects and advantages of the other portions of the gastrostomy tube extension device provided with the engaged portion 72 are the same as the corresponding portion of the gastrostomy tube extension device 20 (first embodiment). In this arrangement, since it is not necessary to provide a separate fixing member, the structure is simplified and low cost to manufacture.

(Seventh Embodiment)

FIG. 17 and FIG. 18 show a state in which a gastrostomy tube extension device 80 according to a seventh embodiment of the present invention is mounted to the gastrostomy tube 10. In the gastrostomy tube extension device 80, the fixing member and the engaging member are formed to be an integrally formed movable fixing member 81 shown in FIG. 19, and the movable fixing member 81 includes a fixing member 82 and an engaging portion 83. The fixing portion 82 is formed with an engaging projection 85 on the outer peripheral surface of the lower end portion of a cylindrical main body 82a. The engaging projection 85 includes two tapered portions 85a formed consecutively in the vertical direction, the diameter of the engaging projection 85 being smaller toward the distal end and gradually increasing toward the proximal end.

The engaging portion 83 includes a holding portion 87 formed of a laterally elongated plate member connected to the upper end of the main body 82a, and a cylindrical engaged portion 88 connected to the center portion of the upper surface of the holding portion 87 as the positioned portion of the present invention. The holding portion 87 is configured in such a manner that the projection 27b is eliminated from the upper engaging portion 27 and a hole (not shown) is formed so as to communicate with the hole of the main body 82a instead of the engaging recess 27a. The cylindrical engaged portion 88 includes an elastic resin material having retractility, and can be moved to a predetermined portion of the engaging stepped portion 24a provided on the rod 21 and engaged.

The structures, effects and advantages of other portions of the gastrostomy tube extension device 80 are the same as the corresponding portions of the gastrostomy tube extension device 20 (first embodiment). Therefore, the same parts are represented by the same reference numerals and descriptions thereof will be omitted. In this arrangement, engagement between the engaging portion 83 and the rod 21 can be easily achieved by pushing the cylindrical engaged portion 88 into the engaging stepped portion 24a. Since the fixing member and the engaging member are integrally formed in the movable fixing member 81, the structure may be simplified and hence the cost may be lowered.

(Eighth Embodiment)

FIG. 20 shows an eighth embodiment of the present invention, and the gastrostomy tube extension device according to this embodiment further includes a clip 89a as a tightening member according to the present invention in addition to the aforementioned gastrostomy tube extension device 80 (seventh embodiment). The clip 89a may be formed of a linear resilient member formed into an omega (Ω) shape as shown in FIG. 21, and is mounted to an engaging projection 85 of the gastrostomy tube extension device 80 attached to the gastrostomy tube 10 via the tube member 11 as shown in FIG. 20. The structures of other portions of the gastrostomy tube extension device provided with the clip 89a are the same as the corresponding portions of the gastrostomy tube extension device 80. Therefore, the same parts are represented by the same reference numerals and description will be omitted.

In this arrangement, the tube member 11 is pressed against the engaging projection 85 by the clip 89a with a stronger force, and is fixedly secured by the fixing portion (82) of the movable fixing member 81. Other effects and advantages of the gastrostomy tube extension device provided with the clip 89a are the same as the aforementioned gastrostomy tube extension device 80. FIG. 22 shows a clip 89b as a modification of the tightening member. This clip 89b is formed of a plate-shaped resilient member formed substantially into a U-shape, and is formed with a substantially circular recess 89c which can press the tube member 11 against the engaging projection 85 at the inner side of the recess. In this arrangement as well, the same effects and advantages as the clip 89a are obtained.

(Ninth Embodiment)

FIG. 23 and FIG. 24 show a state in which a gastrostomy tube extension device 90 according to a ninth embodiment of the present invention is attached to the gastrostomy tube 10. In this gastrostomy tube extension device 90, the fixing member and the engaging member are composed of a movable fixing member 91 shown in FIG. 25 and a tightening screw 99 shown in FIG. 26. The movable fixing member 91 includes a fixing member 92 and an engaging portion 93 as in the aforementioned movable fixing member 81. In this fixing member 92, an engaging projection 95 of the same structure as the engaging projection 85 is formed at the lower end of a cylindrical main body 92a on the outer peripheral surface thereof, and a threaded portion, 99a having an outer diameter larger than that of the main body 92a or the engaging projection 95 is formed on the upper end of the main body 92a. The vertical length of the fixing portion 92 is set to be the same as the vertical length of the fixing portion 82.

The engaging portion 93 includes a holding portion 97 having the same structure as the engaging portion 83, and a cylindrical engaged portion 98. Then, the tightening screw 99 includes a cylindrical metallic screw member which can be screwed with the threaded portion 99a, and is provided with a rough surface for preventing slippage. The tightening screw 99 is screwed onto the threaded portion 99a of the fixing portion 92 whose main body 92a has been press-fitted into the tube member 11, so that the tube member 11 is pressed against the engaging projection 95, whereby fixation between the tube member 11 and the fixing portion 92 is further strengthened. The structures of other portions of the gastrostomy tube extension device 90 are the same as the corresponding portions of the gastrostomy tube extension device 80. Therefore, the same parts are represented by the same reference numerals and descriptions thereof will be omitted. The effects and advantages of the gastrostomy tube extension device 90 are the same as the gastrostomy tube extension device provided with the aforementioned clip 89a or the clip 89b.

The gastrostomy tube extension device according to the present invention is not limited to the aforementioned embodiments, and may be modified in implementation within the technical scope of the present invention. For example, although the engaging stepped portions 24a, 24a are formed on the rods 21, 41 respectively, and the engaging recess 27a which detachably engages the engaging stepped portions 24a, 44a and other parts are provided respectively on the engaging member 23 in the aforementioned respective embodiments, these members can be omitted. In this case, the operator operates the upper engaging portion 27 holding the same with his/her hand. Since the upper engaging portion 27 or the like is configured of the holding portion which is convenient for holding by hand, the operation is facilitated, to the point that even individuals who wish to maintain their gastrostomy tubes themselves may do so in the comfort of their own homes, without the help of doctors or nurses. The holding portion is not limited to the shape as the upper engaging portion 27, and it is also possible to extend the tube member 11 by holding the holding portion 22b or the fixing portion 42 or the like directly by hand and pulling the same.

When providing the engaging stepped portions 24a, 44a, the number thereof is not limited to three or five, and may be other plural numbers or may be single. The spacing of the engaging stepped portions 24a, 44a may be irregular or regular, as is optional for the human body. The cross-sectional shape of the engaging stepped portion 24a or the like is not limited to semi-circle or triangle, and may be various shapes. The engaging stepped portion may be a projection projecting from a predetermined portion of the cylindrical portion instead of a ring-shape, or may be a recess with which the upper engaging portion can engage instead of the ring-shape. The shapes and the materials of other portions which constitute any embodiments of the gastrostomy tube 10 or the respective gastrostomy tube extension device 20 or the like may also be changed as needed without departing from the scope of the invention.

Figure 1:
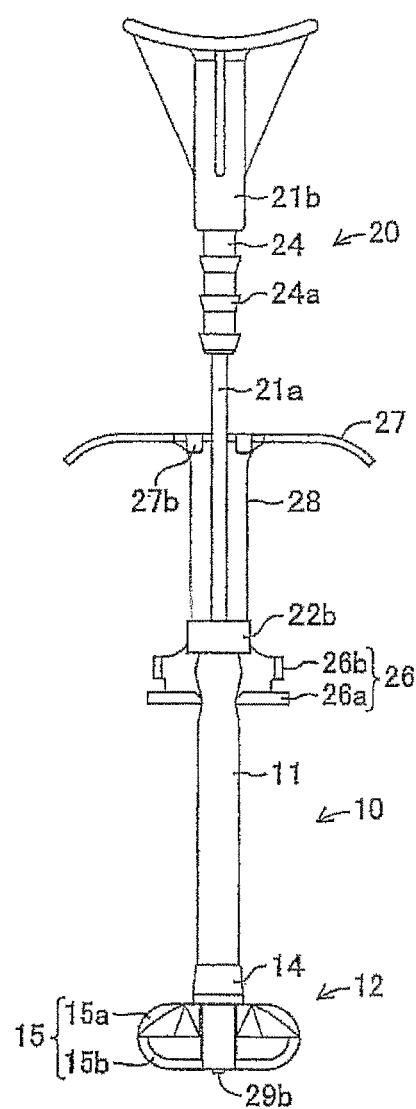
FIG. 1 is a front view showing a gastrostomy tube extension device according to a first embodiment of the present invention is mounted to a gastrostomy tube.
Figure 2:
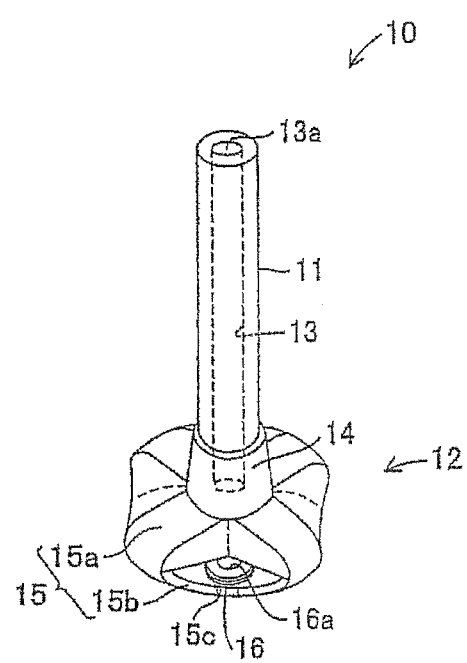
FIG. 2 is a perspective view of the gastrostomy tube.
Figure 3:
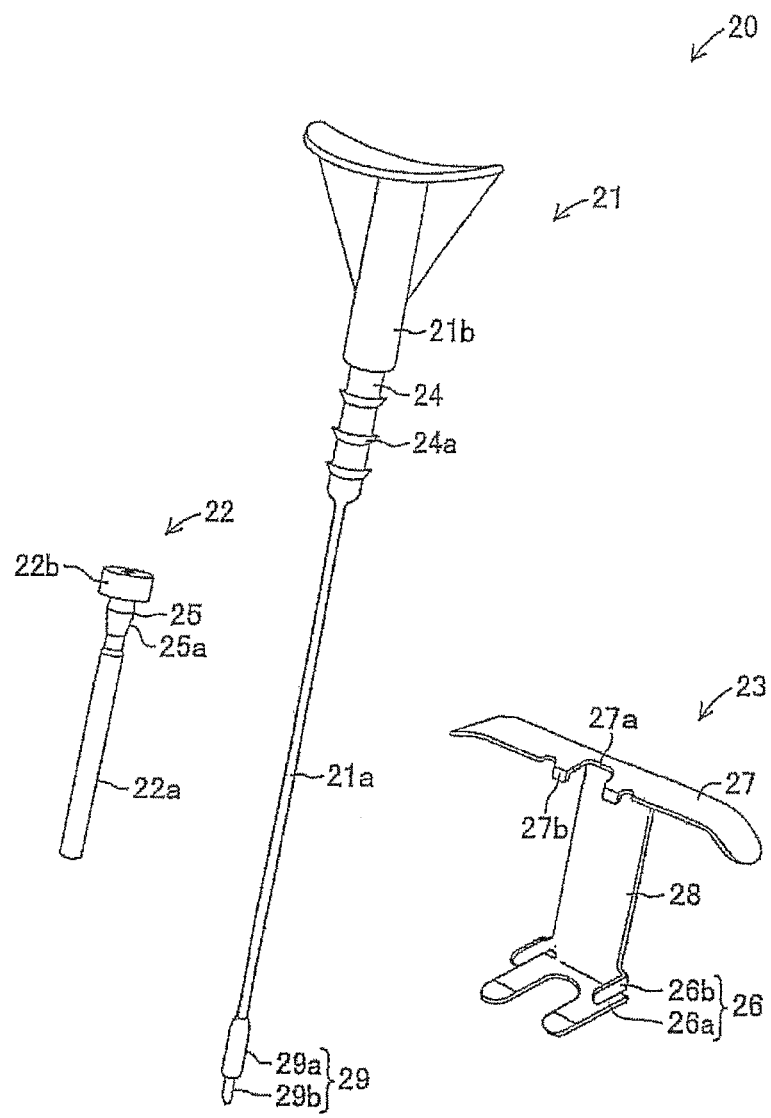
FIG. 3 is an exploded perspective view showing the respective members which constitute the gastrostomy tube extension device.
Figure 4:
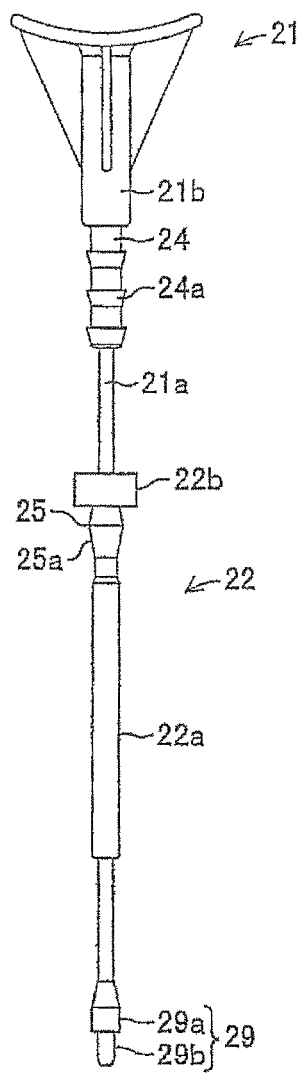
FIG. 4 is a front view showing a fixing member mounted to a rod.
Figure 5:
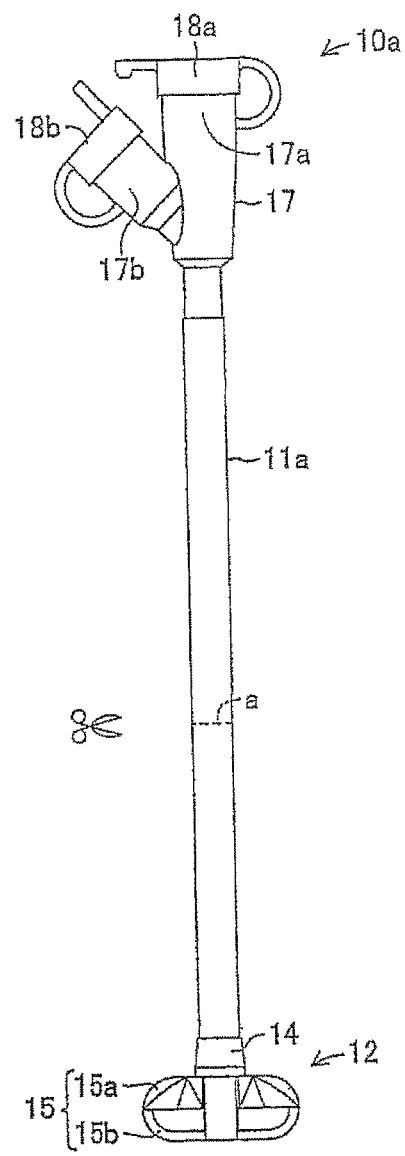
FIG. 5 is a front view showing the gastrostomy tube placed in a patient's body.
Figure 6:
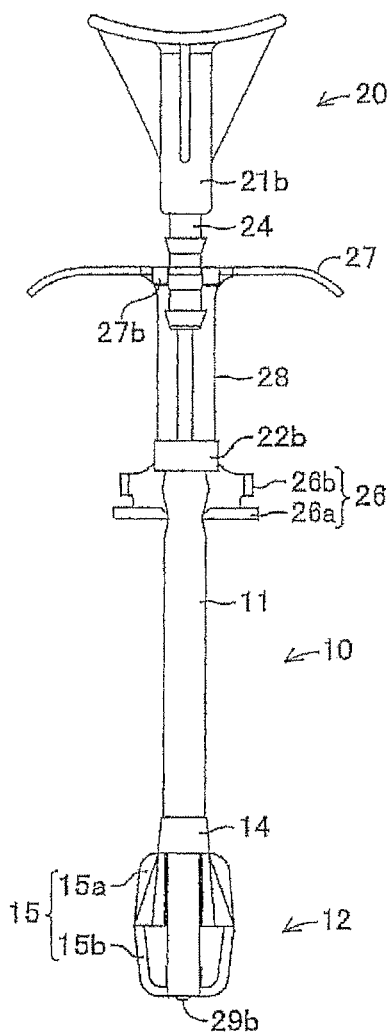
FIG. 6 is a front view showing the gastrostomy tube extended with the gastrostomy tube extension device.
Figure 7:
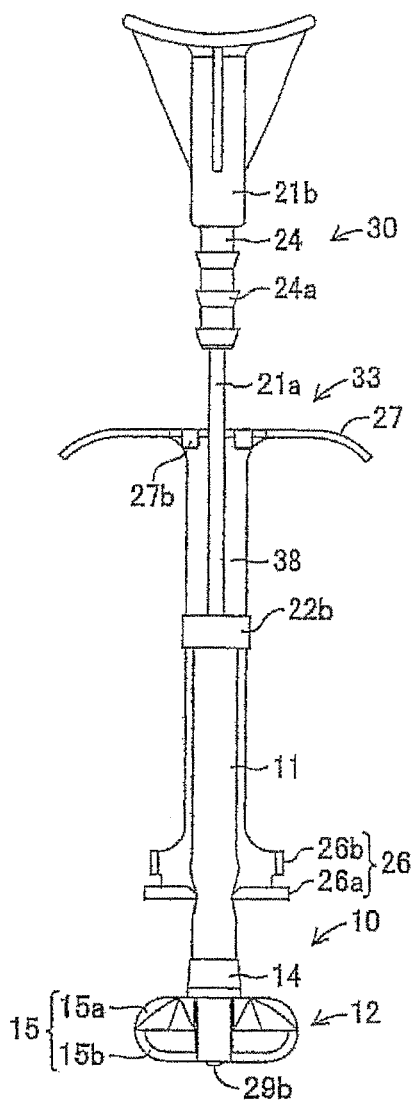
FIG. 7 is a front view showing the gastrostomy tube extension device according to a second embodiment of the present invention, mounted to the gastrostomy tube.
Figure 8:
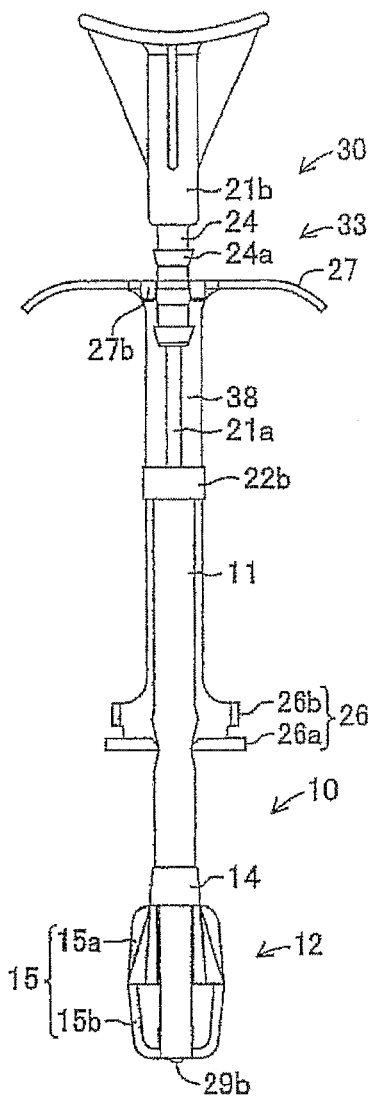
FIG. 8 is a front view showing the gastrostomy tube extended by the gastrostomy tube extending device shown in FIG. 7.
Figure 9:
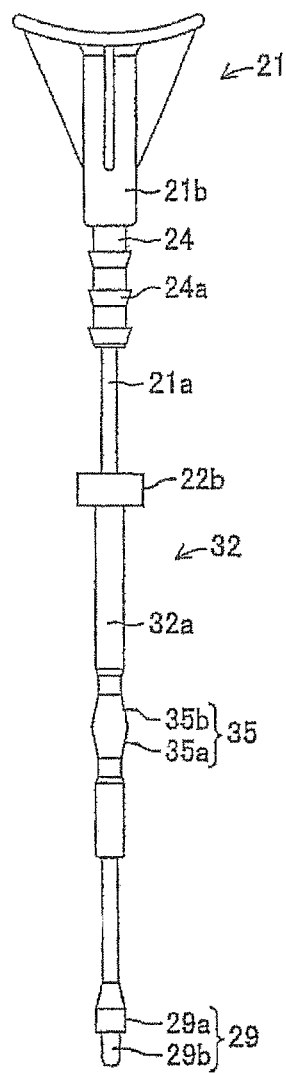
FIG. 9 is a front view showing the mounting member, mounted to a rod provided on the gastrostomy tube extension device shown in FIG. 7.
Figure 10:
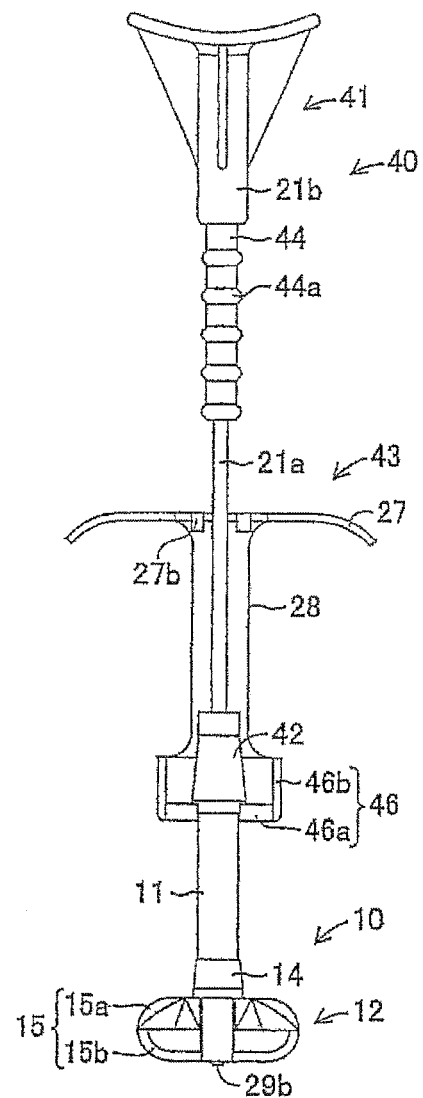
FIG. 10 is a front view showing the gastrostomy tube extension device according to a third embodiment of the present invention, mounted to the gastrostomy tube.
Figure 11:
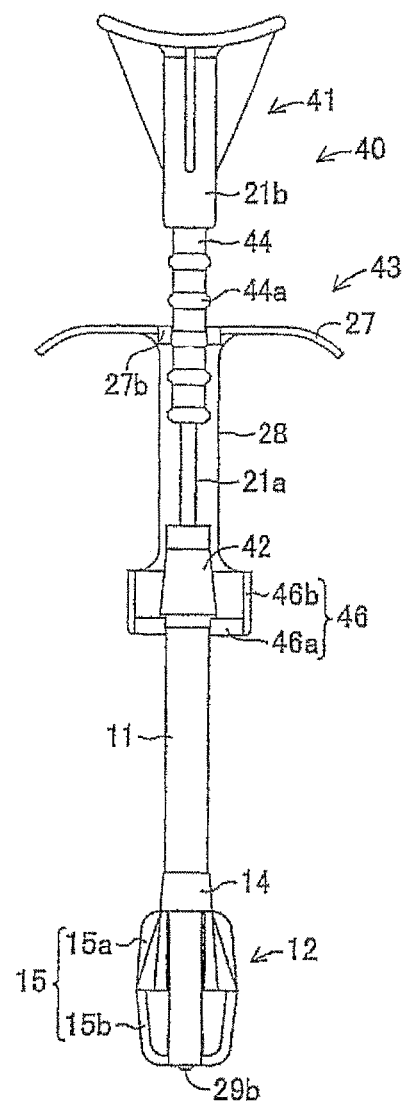
FIG. 11 is a front view showing the gastrostomy tube expanded by the gastrostomy tube extension device shown in FIG. 10.
Figure 12:
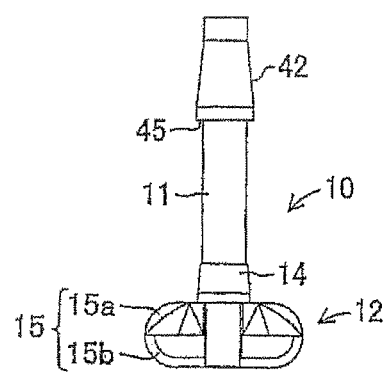
FIG. 12 is a front view showing a fixing portion provided on the gastrostomy tube extension device shown in FIG. 10, fixed to the gastrostomy tube.
Figure 13:
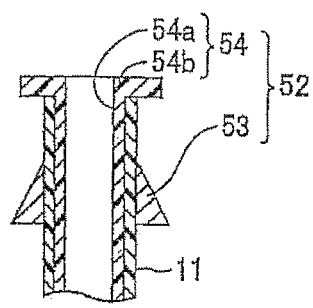
FIG. 13 is a cross-sectional view showing an inner reinforcing member provided on the gastrostomy tube extension device according to a fourth embodiment of the present invention, mounted to a tube member.
Figure 14:
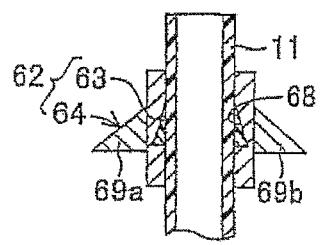
FIG. 14 is a cross-sectional view showing a connector provided on the gastrostomy tube extension device according to a fifth embodiment of the present invention.
Figure 15:
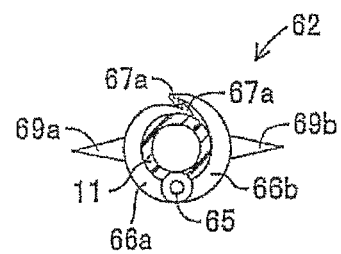
FIG. 15 is a plan view of the connector shown in FIG. 14.
Figure 16:
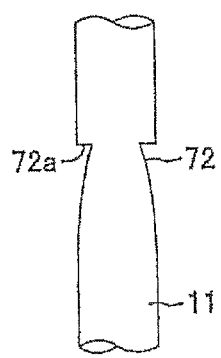
FIG. 16 is a front view showing an engaged portion provided on the gastrostomy tube extension device according to a sixth embodiment of the present invention.
Figure 17:
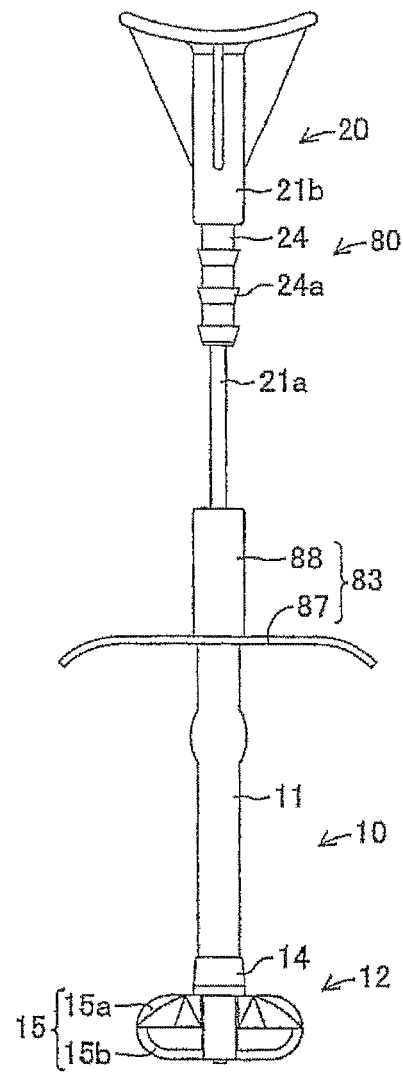
FIG. 17 is a front view showing the gastrostomy tube extension device according to a seventh embodiment of the present invention, mounted to the gastrostomy tube.
Figure 18:
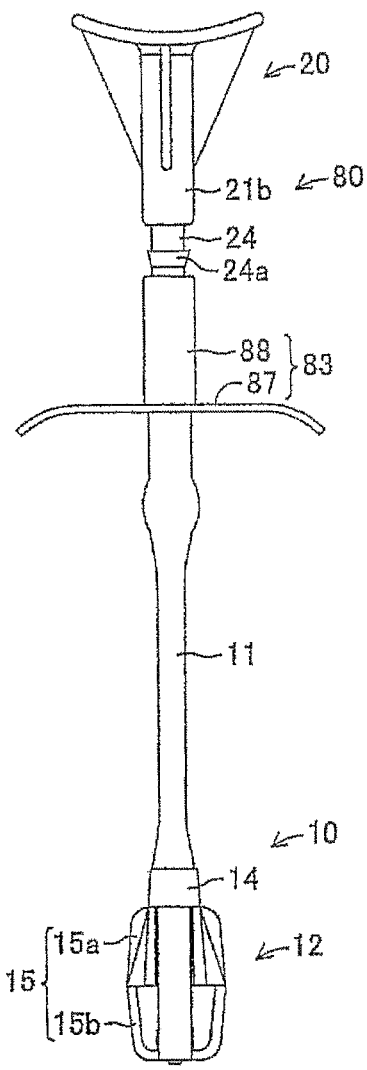
FIG. 18 is a front view showing the gastrostomy tube extended by the gastrostomy tube extension device shown in FIG. 17.
Figure 19:
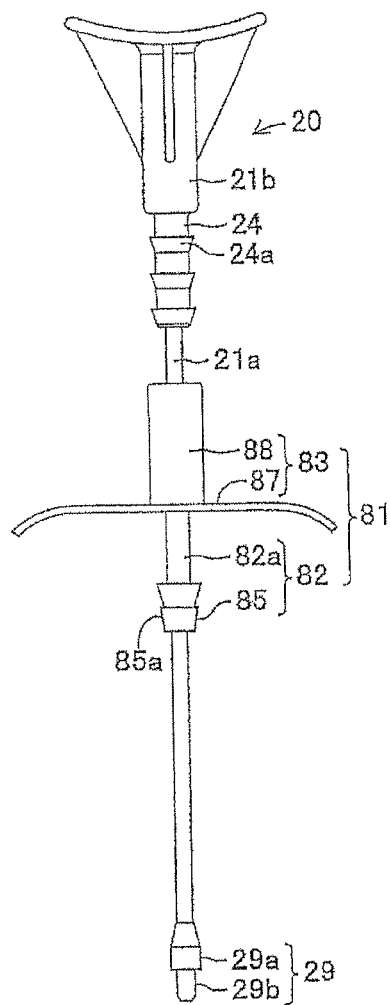
FIG. 19 is a front view showing a movable fixing member mounted to the rod provided on the gastrostomy tube extension device shown in FIG. 17.
Figure 20:
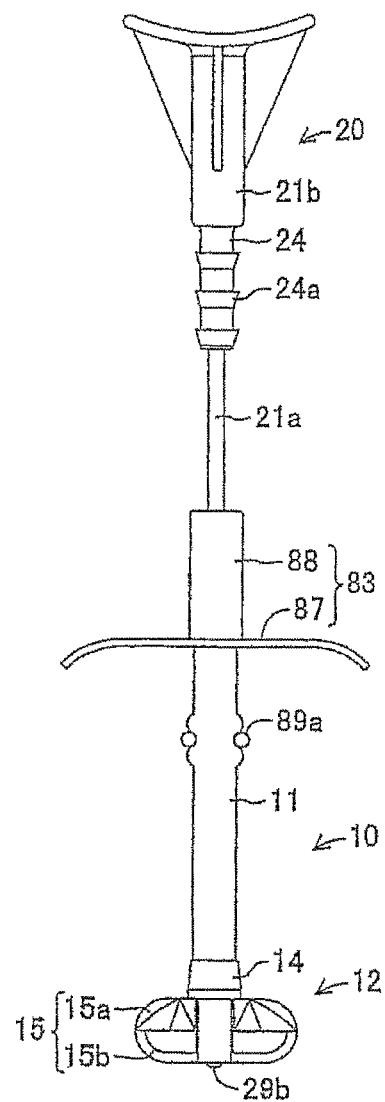
FIG. 20 is a front view showing the gastrostomy tube extension device according to an eighth embodiment of the present invention, mounted to the gastrostomy tube.
Figure 21:
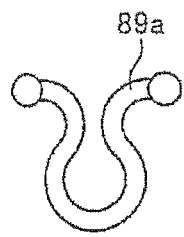
FIG. 21 is a plan view showing a clip provided on the gastrostomy tube extension device shown in FIG. 20.
Figure 22:
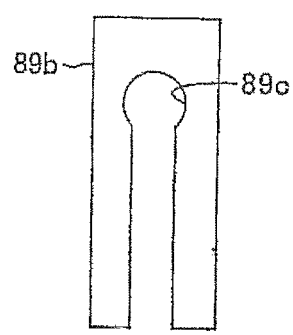
FIG. 22 is a plan view showing the clip according to a modification.
Figure 23:
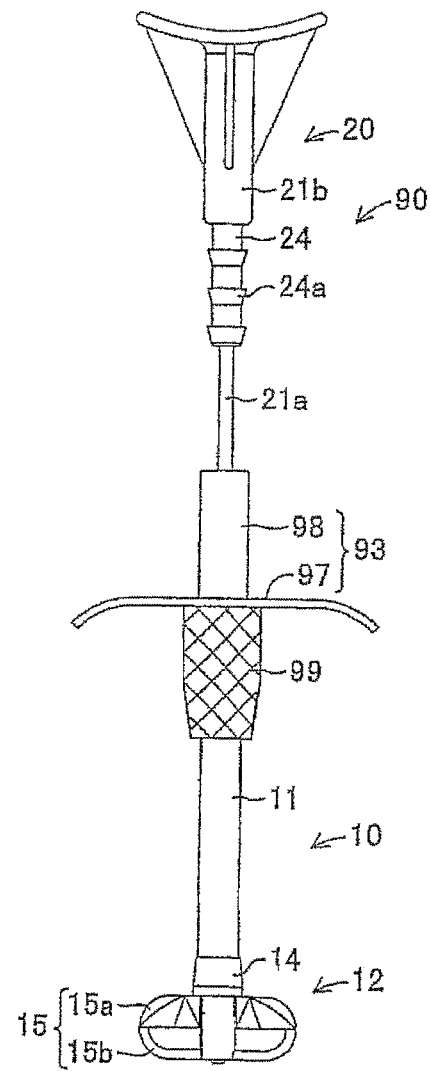
FIG. 23 is a front view showing the gastrostomy tube extension device according to a ninth embodiment of the present invention, mounted to the gastrostomy tube.
Figure 24:
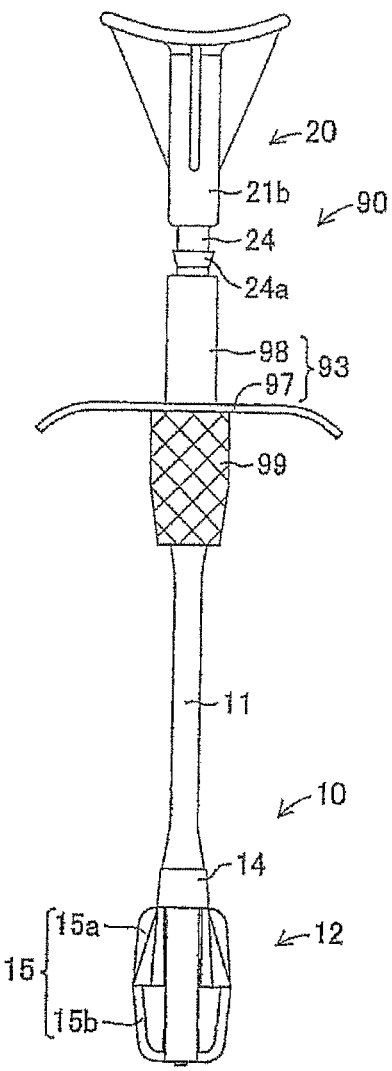
FIG. 24 is a front view showing the gastrostomy tube extended by the gastrostomy tube extension device shown in FIG. 23.
Figure 25:
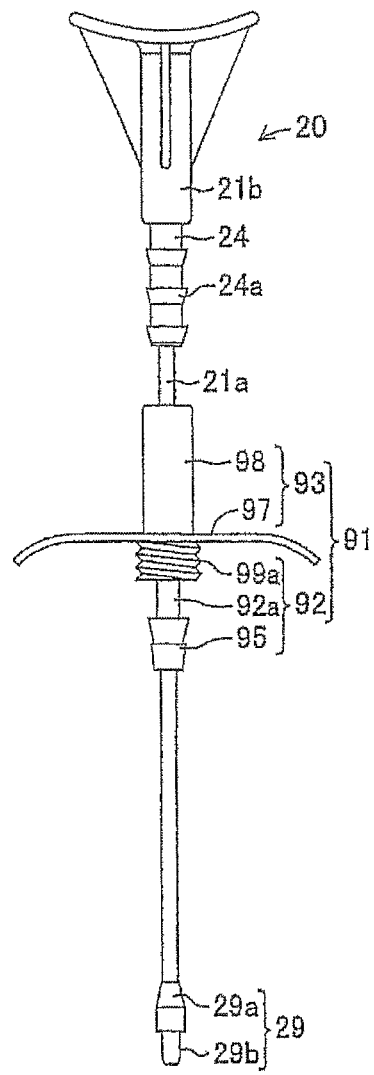
FIG. 25 is a front view showing the movable fixing member mounted to the rod provided on the gastrostomy tube extension device shown in FIG. 23.
Figure 26:
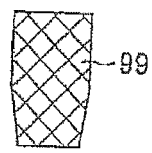
FIG. 26 is a front view showing a tightening screw.

The invention claimed is:

1. A gastrostomy tube extension device used for inserting or taking out a gastrostomy tube, the gastrostomy tube having a stomach interior fixing member and a tube member connected to the stomach interior fixing member, the gastrostomy tube extension device comprising:
    an extender comprising a rod-shaped member which can be inserted into the tube member and can elongate and narrow the stomach interior fixing member by pushing a distal end of the stomach interior fixing member;
    a fixing member which is configured to be inserted within the tube member along a length of the fixing member and a corresponding length of the tube member, and fixed to an outside end of the tube member while allowing the fixing member to move in a longitudinal direction relative to the rod-shaped member;
    an engaging portion which is engageable with the fixing member; and
    an engaging member having a holding portion for holding by hand for operation and elongating the stomach interior fixing member when the holding portion is pulled with the fixing member fixed to the outside end of the tube member,
    wherein the length of the fixing member is in a fixed location relative to the corresponding length of tube member when the holding portion is pulled.

2. The gastrostomy tube extension device according to claim 1, wherein the extender has a positioning portion on a peripheral surface of a proximal portion of the extender, and wherein the engaging member has a positioned portion which can engage the positioning portion and elongate and narrow the stomach interior fixing member when the fixing member is engaged with the engaging portion and the positioning portion is engaged with the positioned portion.

3. The gastrostomy tube extension device according to claim 1, wherein the engaging portion is engaged with the fixing member.

4. The gastrostomy tube extension device according to claim 1, wherein the rod-shaped member directly pushes the distal end of the stomach interior fixing member toward a distal side; wherein the distal side is the distal side of the device; and wherein the engaging member has a lower engaging portion that is engageable with the fixing member.

5. The gastronomy tube extension device of claim 1, wherein the extender includes a main body having an outer peripheral surface, and
   wherein the fixing member is configured to cover the outer peripheral surface when the fixing member is mounted to the main body.

6. A gastrostomy tube extension device used for inserting or taking out a gastrostomy tube into/from a patient, the gastrostomy tube comprising a stomach interior fixing member and a tube member connected to the stomach interior fixing member, the gastrostomy tube extension device comprising:
   an extender comprising an engaging portion and a rod-shaped member which can be inserted into the tube member and can elongate and narrow the stomach interior fixing member by pushing a distal end of the stomach interior fixing member toward a distal side; and
   a fixing member configured for insertion within the tube member along a length of the fixing member and a corresponding length of the tube member, wherein the tube member has a fixing portion on a peripheral surface and proximate an outer end of the tube member, the fixing portion engagable with the engaging portion,
   wherein the length of the fixing member is in a fixed location relative to the corresponding length of the tube member when the rod-shaped member is moved to push the distal end of the stomach interior fixing member toward the distal side.

7. The gastrostomy tube extension device according to claim 6 further comprising a holding portion to be held by hand for operation so that when the extender is inserted into the tube member and the engaging portion is engaged with the fixing portion fixed to the outer end of the tube member, the stomach interior fixing member elongates and narrows when the holding portion is pulled in a proximal direction.

8. The gastrostomy tube extension device according to claim 6, further comprising:
   a positioning portion on a peripheral surface of a proximal portion of the extender, and
   a positioned portion which is capable of engaging the positioning portion so that when the extender is inserted into the tube member and the fixing portion is engaged with the engaging portion and the positioning portion is engaged with the positioned portion, the stomach interior fixing member can be elongated and narrowed.

9. The gastrostomy tube extension device according to claim 8 comprising a plurality of positioning portions disposed along an axial direction of the extender.

10. The gastrostomy tube extension device according to claim 6, wherein the rod-shaped member can directly push the distal end of the stomach interior fixing member; and wherein the distal side is the distal side of the device.

11. A gastrostomy tube extension device for inserting or removing a gastrostomy tube into or from a patient, the gastrostomy tube comprising a stomach interior fixing member and a tube member connected to the stomach interior fixing member and extending through a hole to the outside of the patient's body, the gastrostomy tube extension device-comprising:
   an extender comprising a rod-shaped member which can be inserted into the tube member and can elongate and narrow the stomach interior fixing member by pushing a distal end of the stomach interior fixing member toward a distal portion of the rod-shaped member; and
   a movable fixing member which includes a fixing portion which is capable of being fixed to an outside end of the tube member with a length of the moveable fixing member inserted within a corresponding length of the tube member and the outside end of the tube member located outside of the body, and a holding portion configured to be held by hand and is movable relative to the rod-shaped member along a longitudinal direction of the extender,
   wherein, with the fixing portion fixed to the outside end of the tube member, the length of the moveable fixing member is in a fixed location relative to the corresponding length of the tube member when the movable fixing member is moved along the longitudinal direction.

12. The gastrostomy tube extension device according to claim 11, further comprising a positioning portion on a peripheral surface of a proximal portion of the extender, and wherein the movable fixing member comprises a positioned portion which can engage the positioning portion.

13. The gastrostomy tube extension device according to claim 11, wherein the distal portion is the distal portion of the device; and wherein the rod-shaped member directly pushes the distal end of the stomach interior fixing member.

* * * * *